(12) United States Patent
Fusco

(10) Patent No.: US 8,968,713 B2
(45) Date of Patent: *Mar. 3, 2015

(54) ANTIBACTERIAL HAIR REMOVAL COMPOSITION

(71) Applicant: Normajean Fusco, Unionville, NY (US)

(72) Inventor: Normajean Fusco, Unionville, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/474,102

(22) Filed: Aug. 30, 2014

(65) Prior Publication Data

US 2015/0000049 A1  Jan. 1, 2015

Related U.S. Application Data

(63) Continuation of application No. 13/712,937, filed on Dec. 12, 2012, now Pat. No. 8,828,371.

(51) Int. Cl.
*A61Q 9/04* (2006.01)
*A61K 8/41* (2006.01)
*A61K 8/34* (2006.01)
*A61K 8/92* (2006.01)

(52) U.S. Cl.
CPC ............... *A61K 8/416* (2013.01); *A61K 8/347* (2013.01); *A61K 8/922* (2013.01); *A61Q 9/04* (2013.01); *A61K 2800/74* (2013.01)
USPC .......................................................... 424/73

(58) Field of Classification Search
CPC ... A61K 8/922; A61K 2800/74; A61K 8/416; A61Q 9/04
USPC .......................................................... 424/73
See application file for complete search history.

(56) References Cited

U.S. PATENT DOCUMENTS

| | | |
|---|---|---|
| 3,194,736 A | 7/1965 | Braun et al. |
| 5,980,536 A | 11/1999 | Jamali |
| 6,204,230 B1 | 3/2001 | Taylor et al. |
| 6,241,978 B1 | 6/2001 | Schlaeger |
| 6,312,678 B1 | 11/2001 | Elliott |
| 6,599,513 B2 | 7/2003 | Deckers et al. |
| 7,078,050 B2 | 7/2006 | Fusco |
| 7,507,936 B2 | 3/2009 | Mast et al. |
| 7,759,327 B2 | 7/2010 | Modak et al. |
| 8,038,723 B2 | 10/2011 | Ellis et al. |
| 8,124,577 B2 | 2/2012 | Bernhardt et al. |
| 8,157,814 B2 | 4/2012 | Kelsey et al. |
| 2002/0176876 A1 | 11/2002 | Harris et al. |
| 2005/0019292 A1 | 1/2005 | Acher |

(Continued)

OTHER PUBLICATIONS http://www.cosmetoscope.com/2011/07/olay-smooth-finish-facial-hair-removal-duo/.

(Continued)

*Primary Examiner* — Eisa Elhilo
(74) *Attorney, Agent, or Firm* — Michael E. Zall

(57) ABSTRACT

An antibacterial, non-aqueous liquid hair removing composition. The composition includes a solubilizing oil effective for solubilizing the ingredients, e.g., mineral oil, and an effective antibacterial amount of an antibacterial agent, e.g., triclosan and/or benzethonium chloride. The composition further includes botanical oils and rosins, e.g., soybean oil, gum rosin, rosin esters and titanium dioxide. The composition may also include fragrances and additional bacteriocides, e.g., phenoxyethanol. The hair removal composition is applied to a person's skin, and after a sufficient amount time, removed from the person's skin with the hair entrapped therein.

13 Claims, 3 Drawing Sheets

(56) References Cited

U.S. PATENT DOCUMENTS

| | | |
|---|---|---|
| 2005/0048090 A1 | 3/2005 | Rau |
| 2005/0079189 A1 | 4/2005 | Acher |
| 2005/0085828 A1 | 4/2005 | Acher et al. |
| 2005/0152861 A1 | 7/2005 | Bruening et al. |
| 2006/0135627 A1 | 6/2006 | Frantz et al. |
| 2007/0031360 A1 | 2/2007 | Gupta |
| 2008/0004635 A1 | 1/2008 | McMillan |
| 2008/0255498 A1* | 10/2008 | Houle .............................. 604/20 |
| 2009/0226384 A1 | 9/2009 | Mukhopadhyay et al. |
| 2009/0285871 A1 | 11/2009 | Cunningham et al. |
| 2010/0158986 A1 | 6/2010 | Decker et al. |
| 2010/0172847 A1 | 7/2010 | Modak et al. |
| 2010/0249227 A1 | 9/2010 | Modak et al. |
| 2011/0002971 A1 | 1/2011 | Hassler |
| 2011/0300083 A1 | 12/2011 | Yontz et al. |
| 2012/0258059 A1 | 10/2012 | Wama |

OTHER PUBLICATIONS http://www.silkn.com/Hair_Removal_Cream, Jul. 2012.

http://marketplace.spaelegance.com/browse.cfm/2,535.html, Dec. 2012.

http://allaboutskinvb.net/page/nufree-finipil-hair-removal-system/, Dec. 2012.

http://www.shopvioletwhite.com/servicemenu/waxingdepilationhair.html, Dec. 2012.

* cited by examiner

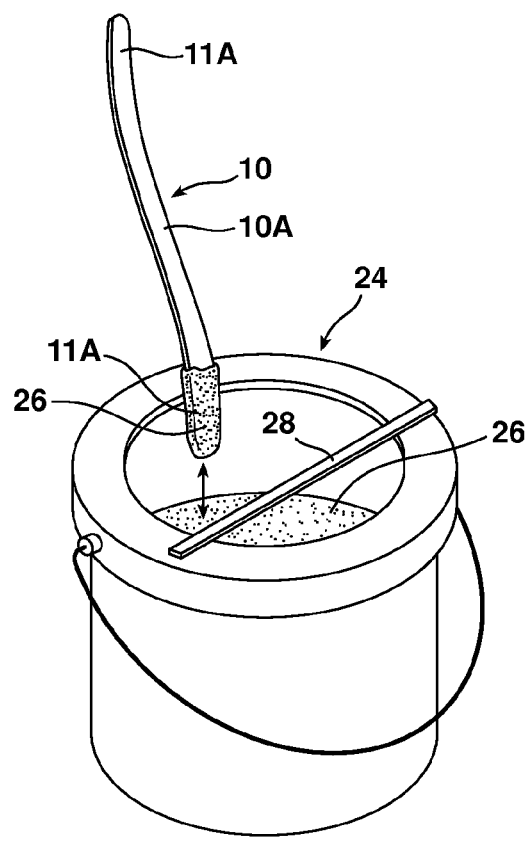
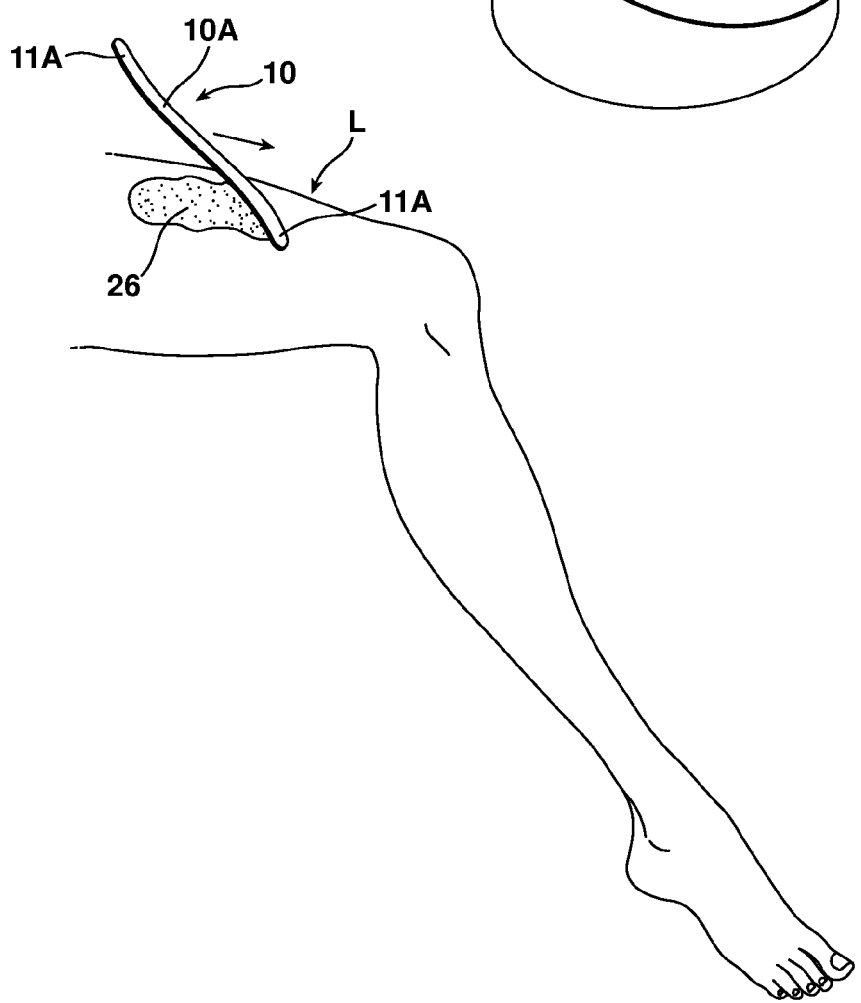

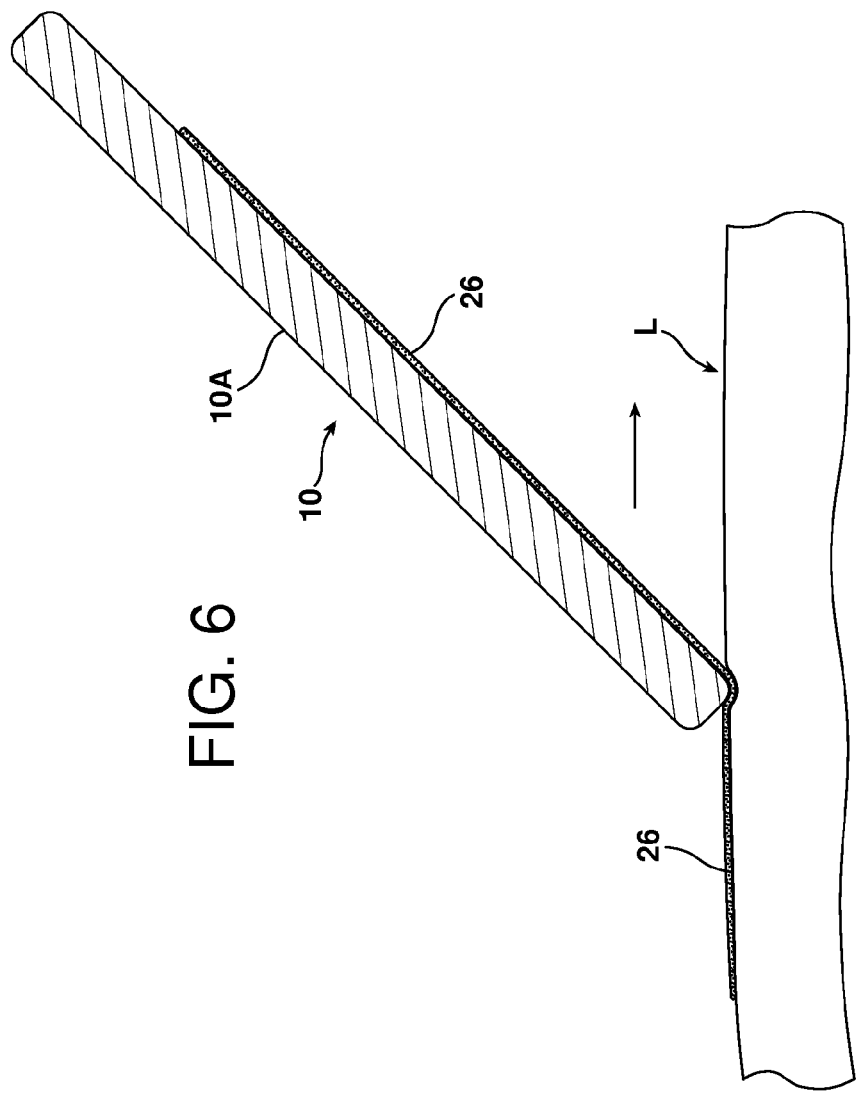
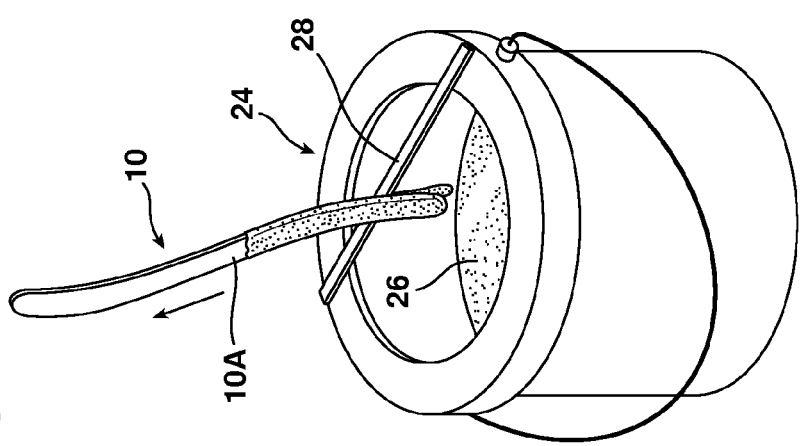

ANTIBACTERIAL HAIR REMOVAL COMPOSITION

RELATED APPLICATIONS

This is a continuation application of U.S. application Ser. No. 13/712,937 filed on Dec. 12, 2012 entitled Antibacterial Hair Removal Composition, which at the date of filing this subject application will issue as U.S. Pat. No. 8,828,371 on Sep. 9, 2014, the entire disclosure of which is incorporated herein by reference.

BACKGROUND OF THE INVENTION

1. Field of the Invention

The present invention relates to a non-aqueous, i.e., anhydrous hair removal composition for the skin and its use. More specifically the hair removal composition includes an antibacterial agent and removes hair gently and under lower temperatures than are required for wax type formulations. The hair removal composition contains mineral oil, soybean oil, gum rosin and rosin esters for removal of the hair and an antibacterial agent. After application to the skin, the hair removal composition is removed with a latex free, non-woven strip material and any remaining composition is removed with a safflower/sunflower erasing lotion.

2. Description of the Related Art

Varieties of methods have been developed for removing unwanted hair from the body. One typical hair removal method is "waxing", a process by which a wax is used to pull unwanted hair out by the root bulb. An applicator is inserted into a bath of hot wax in a wax heater, withdrawn from the bath with the molten wax adhered thereto, and the wax is applied to the skin. The wax cools and hardens on the hair that is to be removed and then peeled off the body, removing the unwanted hair. Waxing is generally painful and uncomfortable for the person undergoing such treatment. In an attempt to minimize the pain, some technicians place a cloth on top of the cooling wax. As the wax cools, it adheres to the cloth and the technician then pulls the cloth to remove the wax and the hair that has been captured by the wax. This is still painful and uncomfortable.

Other systems exist to remove body hair. Depilatory cream shaves been developed that when applied to the skin degrade the hair to break and weaken the hairs. The depilatory and the degraded hair are simultaneously removed from the skin without any mechanical assistance, e.g., by showering. This technique is gentler to the skin but is an inefficient and incomplete system for hair removal. An alternative method is to remove the preparation and hair by means of a spatula, to scrap the cream from the skin, along with broken hairs, and at the same time breaking off weakened hairs, and removing those. This tends to be more effective, but the scraping action can lead to skin coarsening and roughness.

There have also been developed wax free, non-aqueous (anhydrous) liquid depilatories that may be used. These "natural" depilatories consist of botanical oils and rosins. The products do not dry or stick to the skin and gently remove the hair under lower temperatures than are required for wax and wax-like products that utilize constant heating above 160° F. (71° C.). Such products are sold under the NUFREE® brand (Equibal Labs, Unionville, N.Y.) and are used in conjunction with FINIPIL® brand lotion products from Equibal Labs. See also U.S. Pat. No. 7,078,050 to Fusco.

The applicators used for such treatments are usually wooden applicators and are usually thin stick shaped applicators used for eyebrows or flat, spatula type applicators used for the skin surface, e.g., legs, arms, etc. The applicators are typically made of wood and are disposable to prevent contamination. The various State cosmetology boards demand that applicators that cannot be efficiently cleaned and sanitized before the next use be discarded. Thus, most applicators are discarded after use because it is difficult to clean accumulated depilatory and bacteria from such applicators.

If reusable applicators are used, e.g., stainless steel applicators, they are usually cleaned by using heated, harsh chemicals that must be used in a well-ventilated facility. Additionally, such harsh chemical cleaners and conditions are dangerous to customers and spa technicians. Thus, the disposable wooden applicator that is only used once, has become the norm in the industry.

Applicant herein has filed a US Patent Application, U.S. Ser. No. 13/607,698 filed on Sep. 8, 2012, now pending, entitled Compositions For Cleaning Applicator's for Hair Removal Compositions, the entire disclosure of which is incorporated herein by reference. This application is directed to a non-aqueous liquid cleaning composition for applicators, e.g., preferably stainless steel applicators, used for applying non-aqueous hair removal compositions to the skin. The composition includes solubilizing oil, e.g., mineral oil, that is effective for solubilizing the non-aqueous hair removal composition, and includes an antibacterial agent, e.g., triclosan.

The following is a list of US Published applications and US patents related to this art:

U.S. Pat. No. 3,194,736 to Braun et al. discloses a solid depilatory composition that includes a sterol, a non-ionic polyalkenoxy water-in-oil emulsifier, and a solid, inert, organic, filler material that forms a solid base having dispersed therein a solid basic material selected from the hydroxides, carbonates, silicates, and tribasic phosphates of the alkali and alkaline earth metals and guanidine and depilating agents, e.g., substituted thiols. The solid, inert, organic filler material may be a natural or synthetic wax, or solid hydrocarbon, starch, gum or resin.

U.S. Pat. No. 5,980,536 to Jamali describes a rigid, microwavable container and applicator kit for body wax.

U.S. Pat. No. 6,204,230 to Taylor et al. describes aqueous antibacterial compositions that contain a polyhydric solvent, a hydrotrope, a surfactant, an optional antibacterial agent, e.g., triclosan, and water. The compositions provide a substantial reduction, e.g., greater than 99%, in Gram positive and Gram negative bacterial populations within one minute.

U.S. Pat. No. 6,241,978 to Schlaeger describes a cosmetic composition that includes hydrophobic lipophilic materials as the principle vehicle carrying the active ingredients in a continuous solid phase. The composition is formed into a hairstick that is a hair fixative and may include, inter alia, mineral oil, triclosan and fragrance.

U.S. Pat. No. 6,312,678 to Elliott et al. discloses an aqueous rinse-off liquid personal cleansing composition that includes about 1% to about 60% by weight of a water-soluble surfactant, and 0.5% or greater of a water-soluble oil selected. Among the numerous ingredients listed, the compositions can have mineral oil, 2-phenoxyethanol as a preservative and triclosan as an antibacterial agent.

U.S. Pat. No. 6,599,513 to Deckers et al. describes emulsion formulations for topical application which include oil bodies and other ingredients, e.g., triclosan as an antimicrobial, and Neolone as a preservative agent.

U.S. Pat. No. 7,078,050 to Fusco discloses a white cream bacteriostat and fungicide capable of serving as a vehicle for additional medicaments. Also disclosed is a method for blending the ingredients, some of which are not readily compatible with each other.

U.S. Pat. No. 7,507,936 to Mast et al. describes a wax applicator stick scraper for scraping wax, and especially excess wax from a stick used in applying wax to the skin for wax treatment and/or depilation.

U.S. Pat. No. 7,759,327 and US 2010/0249227 to Modak et al. disclose methods and compositions which employ low concentrations of combinations of zinc salts and antimicrobial agents in coatings for medical articles that contact the skin, including depilatories, waxing and razors. The compositions include water-soluble zinc salts, an emollient form based on petrolatum or mineral oil, phenoxyethanol, fragrances, and triclosan and/or phenoxyethanol as antimicrobial or preservative agents.

U.S. Pat. No. 8,038,723 to Ellis et al. discloses an epilatory composition which is rosin-based and applied at body temperature. The epilatory composition is provided as flat strips, comprises a gel-like matrix material, for example a rosin-based or sugar-based material and, mixed with the matrix material, a particulate material, for example colloidal particles of fumed silica, and a polyethylene in the form of a homopolymer.

U.S. Pat. No. 8,124,577 to Bernhardt et al. discloses formulations of personal care compositions and personal care concentrate compositions, e.g., liquid hand soaps, bath and shower washes, shampoos, facial cleaners, that contain sulfoestolides. Such compositions include mineral oil, Neolone, triclosan and fragrances.

U.S. Pat. No. 8,157,814 to Kelsey et al. discloses an S-section plastic spatula design for depilatory application.

US 2002/0176876 to Harris et al. discloses a waterless exfoliant which includes triclosan for antibacterial activity. The treatment includes a first phase composition having antibacterial, anti-inflammatory, humectant, antioxidant and exfoliant ingredients, and a second phase having anti-inflammatory, circulatory enhancement and prolonged moisturizing ingredients.

US 2005/0152861 to Bruening et al. discloses a water-in-oil emulsion antiperspirant compositions containing: (a) an antiperspirant component; (b) a polyol-poly-12-hydroxystearate; (c) an oil component; and (d) water. The antiperspirant may also contain phenoxyethanol and triclosan.

US2005/0019292, US2005/0079189, US 2005/0085828 to Acher et al. discloses an epilatory composition provided as flat strips. The composition comprises a gel-like matrix material, e.g., a rosin-based or sugar-based material, mixed with a particulate material, e.g., colloidal particles of fumed silica.

US 2005/0048090 to Rau disclose an anhydrous self-warming composition that can be included in a depilatory cream. The composition contains at least one inorganic or organic salt, that has a positive heat of solution upon contact with water and produces a warming effect on the skin. Anhydrous carriers are used, e.g., mineral oil, cotton seed oil, castor oil.

US 2006/0135627 to Frantz et al. disclose an aqueous personal care composition comprising titanium dioxide, triclosan, benzethonium chloride, and depilating agents.

US 2007/0031360 to Gupta discloses a depilatory composition applied in liquid form on the surface of the skin, and which is removable by peeling it away from the surface of the skin after setting to a pliable film. The composition includes (i) a pliable film forming agent, (ii) a hair binding agent, and (iii) a hydroxylic matrix forming agent.

US 2008/0004635 to McMillan et al. discloses a spatula for aiding in the removal of a hardened wax from a person's body.

US 2009/0226384 to Mukhopadhyay et al. discloses an antimicrobial composition containing triclosan and at least one functionalized hydrocarbon and/or mixtures containing such functionalized hydrocarbons.

US 2009/0285871 to Cunningham et al. discloses a germicidal wipe having a germicidal solution of at least one peracid, at least one peroxide, and a surfactant. The solution may also have Neolone and Symocide PT.

US 2010/0158986 to Decker et al. discloses personal care compositions and personal care products that impart perceivable aesthetic benefits of increased softness, quietness and drapability to the skin or hair of a user. The compositions may include a mineral oil, fragrances, and Symocide PT.

US 2010/0172847 to Modak et al. discloses preservative or antimicrobial compositions with broad spectrum antimicrobial activity comprising low concentrations of essential oil and a botanical extract in synergistic combination with a fruit acid and alkanediol, and optionally a solvent. The compositions are used in personal care products such as creams or soap products. An antibacterial composition is disclosed that includes botanical extracts and solvents such as vegetable oils, phenoxyethanol as non-alkanediol alcohol at 0.5-4%, and Triclosan for application to varying surfaces.

US 2011/0300083 to Yontz et al. discloses a personal care formulation, that may be anhydrous, comprising antifungal agents and depilatory compounds.

http://www.cosmetoscope.com/2011/07/olay-smooth-finish-facial-hair-removal-duo/discloses from Olay a hair removal cream that is an oil/water emulsion with mineral oil and calcium thioglycolate hydroxide as depilatory.

http://www.silkn.com/Hair_Removal_Cream is a general discussion about depilatories.

Other references include the following:

ASTM E2315-03(2008) *Standard Guide for Assessment of Antimicrobial Activity Using a Time-Kill Procedure*. 100 Barr Harbor Drive, West Conshohocken, Pa., USA. http://www.astm.org/Standards/E2315.htm National Committee for Clinical Laboratory Standards, Standard M7 A5: *Methods for dilution antimicrobial susceptibility tests for bacteria that grow aerobically*. Fifth Edition, National Committee for Clinical Laboratory Standards, Wayne, Pa., 1997.

Winthrop K L, Abrams M, Yakrus M, et. al. *An outbreak of mycobacterial furunculosis associated with footbaths at a nail salon*. New England Journal of Medicine. 2002; 326 (18):1366-1371.

http://wwwnc.cdc.gov/eid/article/14/11/07-1297_article-.htm

Zafar A B, Butler R C, Reese D J, et. al. *Use of 0.3% triclosan (Bacti-Stat) to eradicate an outbreak of methicillin-resistant Staphylococcus aureus in a neonatal nursery*. American Journal of Infection Control. 1995; 23(3): 200-208.

OBJECTS AND SUMMARY OF INVENTION

It is an object of this invention to provide an anhydrous, antibacterial hair removal composition and a procedure for manufacturing and using such composition.

It is yet another object of this invention provide a non-aqueous, liquid hair removal composition that is effective and safe and can be used at relatively low temperatures, e.g., less than 160° F. (71° C.) and have an effective shelf-life.

It is a further object of this invention to provide an anhydrous, antibacterial hair removal composition that does not stick to the skin but to the oils of the hair and is erasable or can be completely dissolved with sunflower, safflower and/or mineral oil and will not harden unless it comes in contact with a hydrous composition, e.g., water.

The foregoing objects are achieved with a non-aqueous antibacterial hair removal composition of this invention that comprises an amount of solubilizing oil, an amount of botanical oils and rosins, e.g., soybean oil, gum rosin, and rosin esters and an amount of an antibacterial agent selected from the group consisting of:

1. About 0.1% to about 0.5% by weight of the hair removal composition of triclosan;
2. About 0.1% to about 2% by weight of the hair removal composition of benzethonium chloride; or
3. Mixtures thereof.

The amounts of botanical oils and rosins, such as soybean oil, gum rosin and rosin esters, in the non-aqueous hair removal composition are sufficient that when the hair removal composition is applied to a person's skin and subsequently removed, hair on the skin is entrapped in the hair removal composition and removed therewith. The amount of solubilizing oil is an effective amount for solubilizing the botanical oils and rosins, e.g., soybean oil, gum rosin, rosin esters and antibacterial agent. The composition may also include additional fragrances and additional bacteriocides, e.g., phenoxyethanol.

The hair removal composition is applied to a person's skin, and after a sufficient amount time, removed from the person's skin with the hair entrapped therein.

The hair removal composition of this invention removes body hair gently and under lower temperatures than are required for wax and wax like products, i.e., less than about 160° F. (71° C.), and has been clinically tested to show a 99.97% reduction of bacteria. The compositions remain bacteria free at low temperatures of use.

Applicant describes herein numerous embodiments of the invention in conjunction with the drawings, which include variations in the different elements of the invention.

BRIEF DESCRIPTION OF THE DRAWINGS

The novel features believed to be characteristic of the present invention, together with further advantages thereof, will be better understood from the following description considered in connection with the accompanying drawings in which several embodiments of the invention are illustrated by way of example. It is to be expressly understood, however, that the drawings are for the purpose of illustration and description only and are not intended as a definition of the limits of the invention.

FIG. 3 depicts contacting a spatula type applicator with the hair removal composition to provide an applicator having the hair removal composition thereon.

FIG. 4 depicts applying the hair removal composition to a person's leg with the applicator.

FIG. 5 depicts a technique for contacting an applicator with the hair removal composition.

FIG. 6 depicts a detailed cross-sectional view applying the hair removal composition to a person's skin with the applicator.

DETAILED DESCRIPTION OF THE INVENTION

Figure 1:
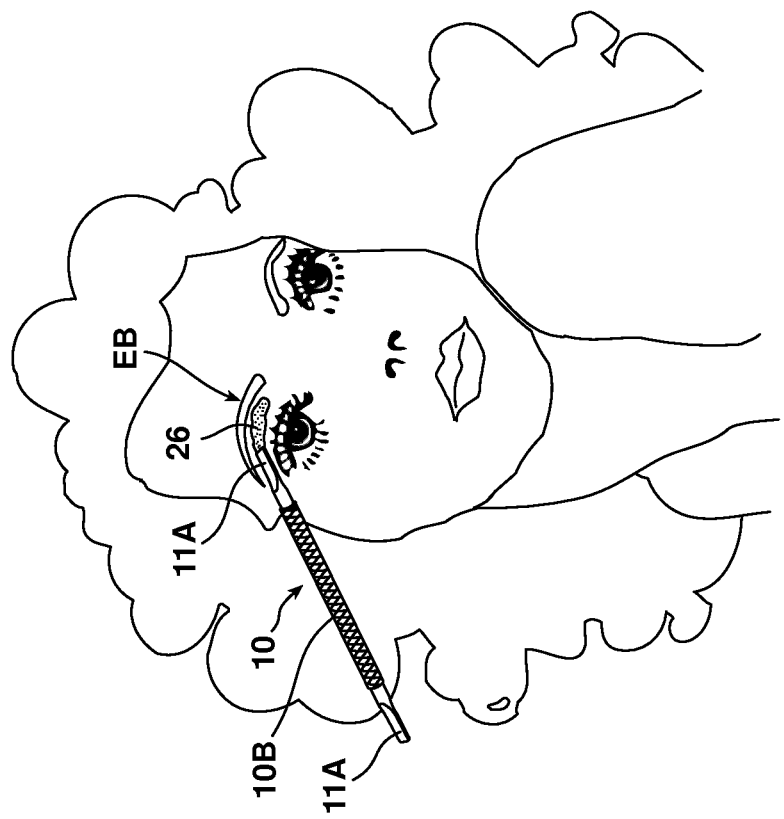
FIG. 1 depicts contacting an eyebrow applicator with the hair removal composition of this invention.

The foregoing objects are achieved with a non-aqueous antibacterial hair removal composition of this invention that comprises an amount of solubilizing oil, an amount of botanical oils and rosins, such as an amount soybean oil, an amount of gum rosin, an amount of rosin esters and an amount of an antibacterial agent selected from the group consisting of:

1. About 0.1% to about 0.5% by weight of the hair removal composition of triclosan;
2. About 0.1% to about 2% by weight of the hair removal composition of benzethonium chloride; and
3. Mixtures thereof.

The amounts of botanical oils and rosins, such as soybean oil, gum rosin and rosin esters, in the non-aqueous hair removal composition are sufficient that when the hair removal composition is applied to a person's skin and subsequently removed, hair on the skin is entrapped in the hair removal composition and removed therewith. The amount of solubilizing oil is an effective amount for solubilizing the botanical oils and rosins and antibacterial agent.

As used herein when the term "weight percent" is used it means the weight of the referenced compound or composition used in the hair removal composition.

Specifically preferred compositions include:

a. About 6.0% to about 8.0% by weight mineral oil, preferably about 6.5% by weight;
b. About 12.0% to about 16.0% by weight soybean oil, preferably about 14% by weight;
c. About 6.0% to about 8.0% by weight gum rosin, preferably about 7.5% by weight;
d. About 68% to about 72% by weight rosin esters, preferably about 71% by weight;
e. About 0.1% to about 0.5% by weight triclosan, preferably about 0.3% by weight;
f. About 0.1% to about 2.0% by weight benzethonium chloride, preferably about 0.2% by weight;
g. About 0.1% to about 0.3% by weight titanium dioxide; and
h. About 0.1% to about 0.2% by weight fragrance.

The composition may also include additional fragrances and bacteriocides, e.g., phenoxyethanol.

The highly preferred hair removal composition of this invention utilizes Food Grade Rosin Ester, WW grade Gum Rosin, Soybean oil, White Mineral Oil, Benzethonium chloride (CAS #121-54-0), Triclosan(5-chloro-2-(2,4-dichlorophenox)phenol) and Titanium Dioxide.

The hair removal composition is applied to a person's skin, and after a sufficient amount time, removed from the person's skin with the hair entrapped therein.

Unlike wax and non-wax related products in the marketplace used for hair removal, the hair removal composition of this invention has been clinically tested and shows a 99.97% reduction of bacteria. The hair removal composition removes hair gently and under lower temperatures than are required for wax and wax like products that need constant heating above 72° C. (161° C.). This relatively high temperature can cause burning of the human skin tissue. Additionally, bacteria can quickly form in such products and be transferred to the skin if used a lower temperatures.

The hair removal composition of this invention remains bacteria free without such high temperatures, stays liquid at body surface temperatures and does not cause lifting of skin tissue when removed. Because of its anhydrous nature, when applied to the body the composition couples and/or bonds to the sebaceous oil secreted but not to the person's skin.

The hair removal composition of this invention is completely dissolved with a safflower/sunflower erasing lotion causing no ill effects to the skin or clothing.

The hair removal composition is applied to the skin, e.g., see FIGS. 1-6. The procedure is similar to waxing with several exceptions that make it safer and less painful. The product is removed with the hair, with a latex free, non-woven strip material. There is no breakage or stinging because the hair removal composition remains in a semi-liquid state and does not dry on the skin.

The hair removal composition of this invention is not a chemical depilatory, which dissolves hair. The procedure is a form of manual depilation with no breakage to the follicles and no risk of cross contamination when used in the salon or professionals office on several clients.

Referring to the Figures, the applicators used in this invention are preferably medical grade stainless steel applicators. Although such material of construction for such applicators is preferred, this invention contemplates any type material, e.g., polymeric, plastic or wooden, that can be effectively and safely used to apply the hair removal composition of this invention. In the Figures two types of applicators are depicted, i.e., a body applicator 10A, and an eyebrow applicator 10B.

The preferred applicators 10 used in this invention are Japanese medical grade stainless steel that can be efficiently cleaned by the compositions and methods described in U.S. Ser. No. 13/607,698 filed on Sep. 8, 2012, now pending, entitled Compositions For Cleaning Applicator's for Hair Removal Compositions.

The hair removal composition of this invention comprises solubilizing oil. The preferred oil for use in the hair removal composition of this invention is mineral oil, i.e., an insoluble cosmetic oil which also acts as emollient for the ingredients. It is a hydrophobic or water repellent ingredient. It is also non-toxic, colorless, transparent, odorless and tasteless, and, when heated, smells like petroleum.

Although mineral oils are preferred, other hydrocarbon oils may be used such as rapeseed oil, theobroma oil, castor oil, jojoba oil, silicone oil, lanolin, olive oil, cocoa butter, and shea butter and various fragrances and essential oils selected to solubilize the specific ingredients in the non-aqueous hair removal composition at relatively low temperatures, i.e., commercially safe temperatures, and capable of holding therein an effective amount of the selected antibacterial agent or agents.

Additional solubilizing oils that may be included in the hair removing composition of this invention are hydrocarbon-based emollients such as petrolatum, fatty ester-based emollients, such as methyl, isopropyl and butyl esters of fatty acids such as isopropyl palmitate, isopropyl myristate, isopropyl isostearate, isostearyl isostearate, diisopropylsebacate, and propylene dipelargonate, 2-ethylhexyl isononoate, 2-ethylhexyl stearate, C(12)-C(16) fatty alcohol lactates such as cetyl lactate and lauryl lactate, isopropyl lanolate, 2-ethylhexyl salicylate, cetylmyristate, oleylmyristate, oleyl stearate, oleyloleate, hexyl laurate, and isohexyllaurate.

In the preferred hair removing composition of this invention the solubilizing oil is mineral oil that is present at from about 6.0% to about 8.0% weight percent of the hair removing composition.

The hair removing composition further includes an effective antibacterial amount of an antibacterial agent. The preferred hair removal composition of this invention includes one or more antimicrobial agents, preferably at a total concentration between 0.01% and 5% by weight, preferably between 0.05% and 3% by weight, and most preferably between about 0.1% and 2% by weight. In the preferred composition, there is from about 0.1% to about 0.5%, preferably 0.3% by weight of triclosan and/or about 0.1% to about 0.5%, preferably about 0.2% by weight of benzethonium chloride, but as high as 2% by weight if triclosan is not used.

Triclosan is a chlorinated diphenyl ether. It is an antimicrobial agent that has been employed for a variety of purposes for more than 20 years. Triclosan is preferred based on its efficacy and its solubility in the selected solubilizing oil. Triclosan has an exceedingly low solubility in water, e.g., 5 to 10 ppm and a relatively high solubility in mineral oil.

Chemical Name: 2,4,4'Trichlorl-2'-Hydroxydiphenyl Ether Phenol 5-chloro-2-(2,4-clichlorophenoxy) CAS Number 3380-34-5

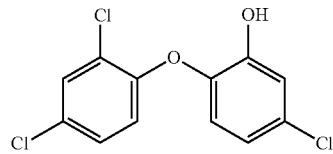 [SMILES: Oc1cc(Cl)ccc1Oc1ccc(Cl)cc1Cl]

Triclosan is relatively non-toxic to humans and other mammals. It is also not found to have any carcinogenic, mutagenic or teratogenic effects. It is used clinically, in oral hygiene products as well as in a wide range of consumer products. Triclosan has a broad range of activity that encompasses many, but not all types of Gram positive and Gram negative non-sporulating bacteria, some fungi and viruses. Triclosan is marketed by Ciba-Geigy of Basle, Switzerland, under the name of Irgasan®.

The hair removal compositions of the invention may alternatively or additionally include one or more antibacterial or anti-microbial agents that can be carried in, e.g., solubilized or emulsified, in the selected solubilizing oil. The agent should have low water content and/or not need water so that it can blend with the selected solubilizing oil.

Examples of agents that may be used include, but are not limited to, chitosan, phenoxyethanol, chlorhexidinegluconate, iodophores, iodine, benzoic acid, dehydroacetic acid, propionic acid, sorbic acid, methyl paraben, ethyl paraben, propyl paraben, butyl paraben, isobutyl paraben, cetrimide, chlorhexidine (free base and/or salts), other biguanides, chloroerosol, chloroxylenol, benzyl alcohol, bronopol, benzalkonium chloride, benzethonium chloride, ethanol, phenoxyethanol, phenyl ethyl alcohol, 2,4-dicholorobenzyl alcohol, thiomersal, clindamycin, erythromycin, benzoyl peroxide, mupirocin, bacitracin, polymixin B, DMDM Hydantoin (Glydant), GERMALL, Kathon CG, Phenonip, miconazole, fluconazole, itraconazole, etcn-alkyl dimethyl benzyl ammonium chloride, n-alkyl dimethyl benzyl ammonium chloride, dialkyl dimethyl ammonium chloride, didecyl dimethyl ammonium chloride, dioctyl dimethyl ammonium chloride, phenolics, iodophors, pine oil, methyl salicylate, morpholine, silver, copper, bromine, and quaternary ammonium compounds, derivatives thereof, and combinations thereof. Antibacterial perfumes such as, for example, thymol, thyme oil, eugenol, clove oil, menthol, mint oil, farnesol, and antibacterial glycerol esters such as, for example, glycerol monocaprate, glycerol monocaprylate, glycerol monolaurate (GML) and diglycerolmonocaprate (DMC) may also be used.

The preferred alternative or additional antibacterial agent is benzethonium chloride. Benzethonium chloride is a synthetic quaternary ammonium salt. This compound is an odorless white solid; soluble in water. It has surfactant, antiseptic, and anti-infective properties, and it is used as a topical antimicrobial agent in first aid antiseptics. It is also found in cosmetics and toiletries such as mouthwashes, anti-itch ointments, and antibacterial moist towelettes. Benzethonium chloride is also used in the food industry as a hard surface disinfectant.

Benzethonium chloride exhibits a broad spectrum of microbiocidal activity against bacteria, fungi, mold and viruses. Independent testing shows that benzethonium chloride is highly effective against such pathogens as methicillin-resistant *Staphylococcus aureus, Salmonella, Escherichia coli, Clostridium difficile*, hepatitis B virus, hepatitis C virus, herpes simplex virus (HSV), human immunodeficiency virus (HIV), respiratory syncytial virus (RSV), and norovirus.

The US Food and Drug Administration (FDA) specifies that the safe and effective concentrations for benzethonium chloride are 0.1-0.2% in first aid products. Aqueous solutions of benzethonium chloride are not absorbed through the skin. It is not approved in the US and Europe for use as a food additive.

In addition to its highly effective antimicrobial activity, benzethonium chloride contains a positively charged nitrogen atom covalently bonded to four carbon atoms. This positive charge attracts it to the skin and hair. This contributes to a soft, powdery after feel on the skin and hair, as well as long-lasting persistent activity against microorganisms.

Benzethonium chloride is available under trade names Salanine, BZT, Diapp, Quatrachlor, Polymine D, Phemithyn, Antiseptol, Disilyn, Phermerol, and others.

The most common forms of bacteria and fungus which are the cause of most irritations or infections are *Staphylococcus aureus* (ATCC 6538); *Pseudomonas aeruginosa* (ATCC 9027); and *E. coli* (ATCC 8739). Common forms of fungi include *Aspergillus niger* (ATCC 16404); and *Candida albicans* (ATCC 10231).

Additional ingredients are added to the hair removal composition of this invention, for example fragrances. Fragrances that may be used in accordance with the present invention include any synthetic as well as natural fragrance and mixtures thereof. A multiplicity of fragrances may be used to achieve the desired effect. Apart from their effects as fragrances, such compounds also may be useful in the instant invention as antimicrobial agents and/or preservatives.

Typically, a fragrance comprises between about 0.1% by weight to about 5.0% by weight of the final composition. Generally, the amount of such fragrance is not critical.

Examples of synthetic fragrances that may be used in accordance with the present invention include without limitation acetanisole; acetophenone; acetyl cedrene; methyl nonyl acetaldehyde; musk anbrette; heliotropin; citronellol; sandella; methoxycitranellal; hydroxycitranellal; phenyl ethyl acetate; phenylethylisobutarate; gamma methyl ionone; geraniol; anethole; benzaldehyde; benzyl acetate; benzyl salicate; linalool; cinnamic alcohol; phenyl acetaldehyde; amyl cinnamic aldehyde; caphore; p-tertiairy butyl cyclohexyl acetate; citral; cinnamyl acetate; citral diethyl acetal; coumarin; ethylene brasslate; eugenol; 1-menthol; vanillin; and mixtures thereof.

Examples of natural fragrances that may be used herein include, without limitation, lavandin; heliotropin; sandlewood oil; oak moss; pathouly; ambergris tincture; ambrette seed absolute; angelic root oil; bergamont oil; benzoin; Siam resin; buchu leaf oil; *cassia* oil; cedarwood oil; *cassia* oil; castoreum; civet absolute; chamomile oil; geranium oil; lemon oil; lavender oil; Ylang Ylang oil; and mixtures thereof.

The preferred fragrance is about 0.1% to about 0.2% by weight Symocide PS ((Phenoxy Ethanol, 1,2 Hexanediol, Decylene Glycol).

The hair removal compositions of this invention may also contain a preservative or preservative system to inhibit the growth of pathogens over an extended period of time. The preferred preservative is Neolone 100, which is phenoxyethanaol available from Dow. Other suitable preservatives for use may include, Kathon CG, which is a mixture of methylchloroisothiazolinone and methylisothiazolinone available from Rohm & Haas; iodopropynylbutylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; imidazolidinyl urea; diazolidinyl urea; and the like. Still other preservatives may include ethylhexylglycerin (Sensiva SC 50 by Schulke&Mayr), phenoxyethanol (Phenoxyethanol by Tri-K Industries), caprylyl glycol (Lexgard O by Inolex Chemical Company, Symdiol 68T (a blend of 1,2-hexanediol, caprylyl glycol and tropolone by Symrise) and Symocide PT (a blend of phenoxyethanol and tropolone by Symrise).

The hair removal composition is applied to a person's skin, and after a sufficient amount time, removed from the person's skin with the hair entrapped therein.

The process of manufacturing a preferred composition comprises:

a. Heating about one-half the amount of soybean oil to a temperature of from about 85° C. (about 185° F.) to about 95° C. (about 203° F.) to produce a heated soybean oil;

b. Mixing the amount of gum rosin in the heated soybean oil to produce an initial emulsified composition;

c. Adding with constant stirring the remaining amount of soybean oil to the emulsified composition to produce a final emulsified composition;

d. Cooling the final emulsified composition a temperature of about 80° C. (about 176° F.) to about 85° C. (about 185° F.) to produce a cooled final emulsified composition;

e. Mixing the amount of rosin esters into the cooled final emulsified composition for a period of at least one hour to produce a mixed composition;

f. Cooling the mixed composition to about 60° C. (about 140° F.) to about 70° C. (about 158° F.) to produce a cooled mixed composition;

g. Mixing the amount of mineral oil, the amount of triclosan, and the amount of benzethonium chloride to form a second emulsion;

h. Mixing the second emulsion with the cooled mixed composition for a period of from 2 to 6 hours and subsequently cooling to room temperature to produce the non-aqueous, antibacterial hair removal composition.

Referring to FIGS. 1-6, an applicator 10 is provided for applying the hair removal composition 18 to the skin, e.g., the leg L or eyebrow EB. Preferably, the applicator 10 is made of medical grade stainless steel. The use of a stainless steel applicator 10 also permits a finer coating on the applicator 10 thus using less hair removal product 26. However, any of the well-known wood type applicators may be used.

Initially a sterile applicator 10 is contacted with the hair removal composition 26 to provide an applicator 10 having the hair removal composition on the tip 11A of the applicator 10. The applicator 10 is then used for applying the hair removal composition 26 to a person's skin.

Referring to FIGS. 1, 3 and 5, the applicator 10 is then dipped in a hair removal composition 26 held in heated container 24 and the excess is removed by passing the applicator 10 over the scraper bar 28 over the opening of container 24. In FIGS. 1, 3 and 5, a heater 24 is shown into which a hair removal product 26 is placed, e.g., a can containing the product, so that it can be heated. The excess hair removal product is scraped from the applicator 10 by a scraper bar 28, which can be fitted over an arc of the peripheral edge of the can or heater.

Figure 2:
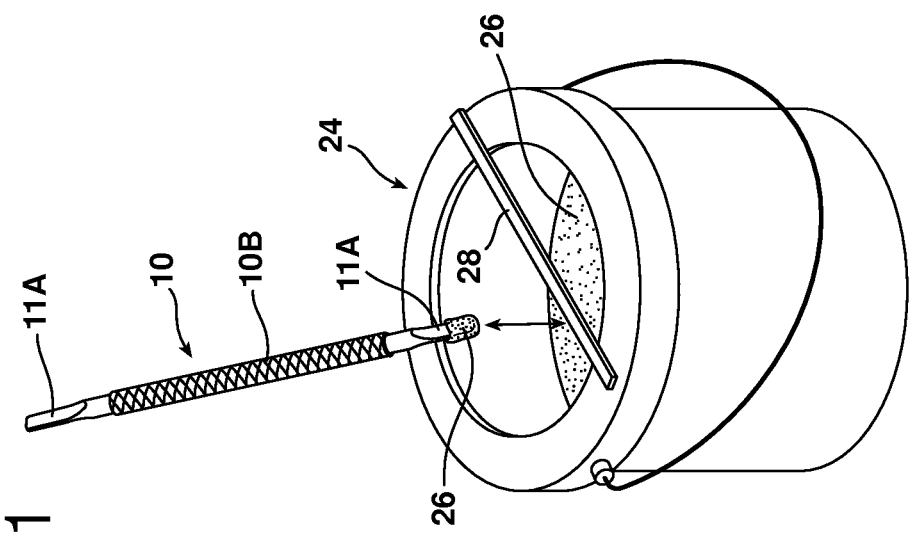
FIG. 2 depicts applying the hair removal composition to a person's eyebrows with the applicator.

In FIGS. 1 and 2, the eyebrow applicator 10B tip 11A is used to apply the hair removal composition 26 to the eyebrow EB for subsequent removal from the eyebrow EB (not shown). In FIGS. 3-6, the body applicator 10A, which has a curved surface on both ends 11A, is used to apply the hair removal composition 26, for example, to the leg L for subsequent removal from the eyebrow leg L (not shown) of the hair removal composition 26 and the hair.

More specifically, referring to FIGS. 1 and 2, when the technician is ready to use the eyebrow applicator 10B the applicator tip 11A is "tapped" into the hair removal composition 26 in heater unit 24 until a little round ball of product is formed on the tip 11A. The tip is then contacted with the scrapper bar 28 to produce a small "ball of product" of sufficient amount to do the whole eyebrow EB. The technician then applies a nice smooth path of product on the hair that needs to be removed. The applicator 10 applies a thin, even coating of hair removal product 26 on the skin with no harm to the skin.

Again, more specifically, referring to FIGS. 3-6, when the technician is ready to use the body applicator 10A he/she will dip the applicator into the heated hair removal composition 26. The tip 11A of the applicator 10A is then scrapped across the scraper bar 28 on one side of the applicator tip 11A (FIG. 5) to clean that side of the applicator tip 11A. The technician then applies the other side of the tip 11A having the hair removal product thereon to the skin, e.g., leg L, at between a 45° angle and 90° to the skin L applying the product in a thin layer onto the skin L.

After application of the hair removal composition 26 to the body, the applicator 10 is contaminated with a residual amount of the hair removal composition 26, primarily but not solely on the tip 11A. At this point, if the applicator is disposable, e.g., wood, the applicator is discarded. Alternatively, and preferably, the applicator is a stainless steel applicator and cleaned in accordance with the compositions and procedures described in U.S. Ser. No. 13/607,698 filed on Sep. 8, 2012, now pending, entitled Compositions For Cleaning Applicator's for Hair Removal Compositions.

The heater cup 24 for the hair removal composition is designed to keep the temperature of the hair removal composition between 125° F. (52° C.) and 140° F. (60° C.) and is heated by electricity from a 12 volt, 2.5 amp source.

The hair removal composition of this invention is antibacterial and liquid at low temperatures. The compositions do not require the use of pasteurizing temperatures necessary for wax or resin based hair removal compositions typically used in "waxing" processes. The hair removal compositions of this invention may be used below 160° F. (71° C.) and maintain a relatively long shelf life.

The hair removal compositions of this invention never dry when maintained at body temperature. The composition is anhydrous and does not stick to the skin but binds or coalesces with the oils of the hair. This is unique compared to other waxes or wax like products. The composition is erasable, i.e., it can be completely dissolved with sunflower, safflower or mineral oil and will not harden unless it comes in contact with a hydrous element.

This new formula goes beyond any waxlike products on the market in that it not only has all the attributes above but it is an antibacterial anhydrous formula.

In summary, the hair removal composition of this invention provides a combination of benefits and advantages over the known hair removal compositions, in particular:
  100% botanical—no chemicals, no sugar, no wax.
  Bonds with the hair only
  Less painful to use than other formulations.
  Removes the entire hair, root, bulb and shaft each time—no stubble.
  Liquifies at body temperature, easy super thin application that gives more value per ounce. Stays Liquid. Never dries.
  No prior preparation. Applies easily—no waiting. Put it on, take it off.
  It's odorless.
  Can be used for 98% of the body.
  The only Antibacterial/Antimicrobial & Anhydrous hair removal system.
  Is erasable. Easily removed from skin & hair with Erasing Lotion if there is an error.
  Clean hair removal station easily with Erasing Lotion.

EXAMPLES

Antibacterial Activity

The following methods were used in the preparation and testing of the antibacterial activity of the Hair Removal Compositions of this invention:
Determination of Rapid Germicidal (Time Kill) Activity of Antibacterial Products.

The activity of the antibacterial hair removal compositions of this invention were measured by the time kill method, whereby the survival of challenged organisms exposed to an antibacterial test composition were determined as a function of time. In these tests, a diluted aliquot of the hair removal composition was brought into contact with a known population of test bacteria for a specified time at a specified temperature. The test hair removal composition was neutralized at the end of the time period, which arrests the antibacterial activity of the composition. The percent or, alternatively, log reduction from the original bacteria population was calculated. This time kill method of testing the activity of antibacterial products is known to those skilled in the art.

The compositions may be tested at any concentration from 0-100% by weight. The choice of which concentration to use was at the discretion of the investigator, and suitable concentrations are readily determined by those skilled in the art. For example, viscous samples usually are tested at 50% by weight dilution, whereas non-viscous samples are not diluted. The test sample was placed in a sterile 250 ml (15.26 cubic inches) beaker equipped with a magnetic stirring bar and the sample volume was brought to 100 ml (6.102 cubic inches), if needed, with sterile deionized water. All testing was performed in triplicate, the results were combined, and the average log reduction was reported.

The choice of contact time period was also at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25° C. (about 77° F.).

The bacterial suspension, or test inoculum, was prepared by growing a bacterial culture on any appropriate solid media (e.g., agar). The bacterial population was then washed from the agar with sterile physiological saline and the population of the bacterial suspension was adjusted to about 10(8) colony forming units per ml (cfu/ml).

The table below lists the test bacterial cultures used in the following tests and includes the name of the bacteria, the ATCC (American Type Culture Collection) identification number, and the abbreviation for the name of the organism used hereafter.

ASTM E2315, *Standard Guide for Assessment of Antimicrobial Activity Using Time-Kill Procedure*, is incorporated herein by reference. This procedure was used to assess the in vitro reduction of a microbial population of test organisms after exposure to a test material.

Example 1

Test Organism(s)

S. aureus ATCC 6538
Purpose:
Determination of the efficacy of hair removal composition of this invention as described herein ("NN-3") that includes 0.3% by weight triclosan and 0.5% by weight benzethonium chloride.
Experimental Design:
Test 1: Time Kill Study Using 1 Part Inoculum: 9 Parts Test Product, a Modification of ASTM Method E2315.
The following test organisms were used:
1) S. aureus ATCC 6538
Note: inoculum is increased 10× compared to previous experiment to determine if the percentage reduction is antibacterial (≥99.9%)
A 0.09 ml (0.005492 cubic inch) aliquot of NN-3 hair removal composition was warmed to 52° C. and mixed with 0.01 ml (0.0006102 cubic inch) of an overnight culture diluted to 0.45 OD at 600 nm, and mixed for 15 seconds. After the time has elapsed, 4.9 ml (0.299 cubic inch) of D/E broth was added to the reaction tube to quench antimicrobial the activity. A secondary 1:100 dilution with D/E broth (0.02 ml to 1.98 ml D/E broth) and 0.5 ml aliquots of the last dilution are plated. The TSA plates were incubated for 24-48 hours at 35° C. to 37° C. As a control, 0.09 ml of NN-3 hair removal composition without triclosan and benzethonium chloride was substituted for the test product and was processed in the same manner as the test groups with an extra 1:10 dilution of which, a 0.5 ml aliquot was plated. A saline+D/E broth un-inoculated blank was also subcultured to ensure sterility of the media and technique.
Note: if applicable, the different test samples were tested alternately to eliminate an order bias, e.g. sample X was tested followed by sample Y and then sample Z and back to sample X, etc.
Calculations:
# of CFU/control sample: CFU/plate×10,000
# of CFU/test sample: CFU/plate×1000
Zone of Inhibition Assay Using S. Aureus ATCC 6538
An overnight culture of S. aureus was diluted to 0.46 OD at 600 nm and then further diluted $10^{-2}$ for inoculation of TSA plates as follows: 0.5 ml was spread across the surface of a sterile TSA plate and allowed to dry.
Materials:
  1. Cole-Parmer D/E Neutralizing Broth Lot No: 10162 Expiration Date: 5/2013
  2. NN-3 including 0.3% triclosan+0.5% (w/w) benzethonium chloride (Lonzagard BZT);
  3. Difco TSA
  4. Cole-Parmer TSB
Results:
Time Kill Study.
v. S. aureus ATCC 6538
Control 1 # of CFU/plate: 114 # of CFU/control sample: $1.1 \times 10^6$
NN-3 Test 1 # of CFU/plate: 1 # of CFU/test 1 sample: $1.0 \times 10^3$
NN-3 Test 2 # of CFU/plate: 4 # of CFU/test 2 sample: $2.0 \times 10^3$
NN-3 Test 3 # of CFU/plate: 1 # of CFU/test 2 sample: $1.0 \times 10^3$
Average counts/sample: $1.3 \times 10^3$
Average reduction: 99.988%
Blank Sample # of CFU/plate: 0
Conclusions: The results of a repeat test of the combination of 0.3% triclosan+0.5% BZT match previous results, i.e., a reduction in challenge organism counts of ≥99.9%.
Modification of ASTM E2315

TABLE 1

Compendium of NN-3 hair removal composition time kill results.

| Test organism | Control cfu/sample | NN-3 $\overline{X}$ cfu/sample | % reduction |
|---|---|---|---|
| S. aureus ATCC 6538 | $1.1 \times 10^6$ | $1.3 \times 10^3$ | 99.99% |

Example 2

Test Organism(s)

S. aureus ATCC 6538
Experimental Design:
Project Title: Determination of the Antimicrobial Activity of Hair Removal Composition Using Time Kill Method ASTM E2315-03.
Description of the Study
The risk of transmission of pathogens from one person to another is a concern in the beauty salon industry where products, equipment and tools of the trade may be re-used on multiple clients. Health departments and other regulatory bodies require that stringent hair removal and sanitization procedures are carried out on any non-disposable equipment or materials such as scissors and re-useable product applicators in between clients. In some cases, equipment is "double dipped" in materials in between clients and it then becomes necessary to validate that these materials are self-disinfecting. An example of such a antimicrobial material is "Barbicide®" that is used to disinfect combs and scissors in between clients.
This study was designed to determine if the preferred hair removal composition of this invention (NN-3) is self-disinfecting when used as directed. In the salon setting, the hair removal composition is applied to the skin from a heated reservoir using either a wood applicator that is discarded after each client or a stainless steel applicator that is cleaned and disinfected in between clients.
In this study we investigated whether pathogens could survive in sub-pasteurization temperatures (68° C. (154. ° F.) to 72° C. (161. ° F.)) in the hair removal composition of this invention containing triclosan.
General Description of the Assay
A modification of a time kill assay based on ASTM method E2315-03 and standardized microbiological testing was used to determine the efficacy of a the hair removal composition of this invention containing triclosan as the antibacterial agent.
An aliquot of the composition was heated to 68° C. to 72° C. and inoculated with a known amount of challenge organism. After a 15 second interval the antimicrobial action was stopped using a validated drug inactivating medium. As a control, a non-antimicrobial version of hair removal composition, i.e., without triclosan was used at 45° C. (113° F.) in an otherwise identical test set-up. After appropriate dilutions and plating, the surviving organisms were enumerated and the percentage reduction in the test group was determined by comparison to the control.

This model was designed to determine the capability of the hair removal composition of this invention in rapidly inactivating any organisms that may be introduced into the heated reservoir when the applicator was dipped into it. If the hair removal composition of this invention demonstrates rapid and broad spectrum antimicrobial activity. This indicates that the risk of cross contamination among clients may be reduced or eliminated in the salon setting.

Materials and Methods

Materials:
1. Cole Parmer trypticase soy agar (TSA)
2. Cole-Parmer trypticase soy broth (TSB)
3. Sabouraud dextrose agar (SDA)
4. Sabouraud dextrose broth (SDB)
5. Cole-Parmer D/E Neutralizing Broth
6. Hair removal composition (triclosan-free; Lot # EQL-NN-0)
7. Hair removal composition (Lot # EQL-NN-1); custom prepared with 0.3% (weight/weight) triclosan.
8. Gamma sterilized culture tubes
9. Digital timer
10. Spectronic® 20
11. Autoclave
12. Vortex mixers
13. Gamma sterilized serological pipettes
14. Micropipettes and steam sterilized tips
15. Gamma sterilized Petri dishes
16. Lab magnetic stirrer/hotplates
17. ASTM Traceable® digital temperature probes
18. Constant temperature incubators
19. Test Organisms:
  a. *Staphylococcus aureus* ATCC #6538
  b. *Pseudomonas aeruginosa* ATCC #9027
  c. *Escherichia coli* ATCC #8739
  d. Methicillin Resistant *Staphylococcus aureus* ATCC #33592
  e. *Aspergillus brasiliensis* ATCC #16404
  f. *Candida albicans* ATCC #10231

Methods

Experimental Setup for ASTM Method E2315-03 In Vitro Time Kill Assays:

A 0.09 ml aliquot of test hair removal composition of this invention was warmed to 70° C.±2° C. was mixed with 0.01 ml of an overnight culture of the challenge organism (diluted to 0.45 OD at 600 nm with either TSB for bacteria or SDB for yeast and mold), and mixed thoroughly using the tip of the inoculating pipette for 15 seconds. After the time has elapsed, 4.9 ml of D/E broth was added to the reaction tube to quench the antimicrobial activity. A secondary 1:100 dilution was carried out using D/E broth 0.02 ml to 1.98 ml D/E broth—except for *C. albicans*—see raw data) and 0.5 ml aliquots of this dilution were plated (TSA is used for bacteria and SDA for yeast and mold).

The plates were incubated for 24-48 hours at 35° C. to 37° C. for bacteria and yeast and for 5 days at 21° C. for fungus. Triplicate samples were used in the test group. As a control, 0.09 ml of the hair removal composition without triclosan was substituted for the test product and processed in the same manner as the test groups with the following exceptions:
  a) the control was kept at 45° C., and
  b) an extra 1:10 dilution was carried out of which a 0.5 ml aliquot was plated.

A medium+D/E broth uninoculated blank was also subcultured to ensure sterility of the media and technique.

Note: if applicable, the different test samples were tested alternately to eliminate an order bias, e.g. sample X was tested followed by sample Y and then sample Z and back to sample X, etc.

Validation of Test Parameters:

Demonstration of inactivation of residual triclosan in the first and second dilutions so that carry-over of drug does not produce a false negative. Briefly, D/E broth was inoculated with approximately 100 CFU/ml of either *Staphylococcus aureus* ATCC #6538 or *Pseudomonas aeruginosa* ATCC #9027 and added to tubes containing 0.1 gram of test product. As a control, 0.1 gram of TSB was substituted for the test product. After vortexing the tubes at high speed, a 0.5 ml aliquot was removed from the tube and plated on the appropriate agar. The microbial counts recovered from the test and control groups were compared. If there is less than a 5% difference between test and control groups, the inactivation of the triclosan was considered to be successful and therefore eliminates the possibility of a false negative due to potential carry over of the drug in the actual assay.

Zone of Inhibition Assay:

An overnight culture of MRSA ATCC 3592 is diluted to 0.46 OD at 600 nm and then further diluted $10^{-2}$ to obtain approximately $3 \times 10^6$ CFU/ml for the inoculation of TSA plates as follows: a 0.5 ml volume was spread across the surface of a sterile TSA plate and allowed to dry. A 7 mm well was made in the center of the agar plate and approximately 200 microliters of either the test or control (no antibacterial agent) hair removal composition was pipetted into the well. The plates were incubated at 37° C. for 24 hours and the zones of inhibition were determined by measuring the diameter of the clear circular area around the product filled well.

Calculations:

# of CFU/control sample: CFU/plate×10,000 # of CFU/test sample: CFU/plate×1000

The number of colony forming units recovered from a test sample was calculated as follows:

# of CFU/sample=[CFU/plate]×[dilution factor]

For example:

A test subculture plate inoculated with 0.5 ml of a 1:1000 dilution of the recovery medium contains 5 CFU therefore:

# of CFU/sample=[5]×[1000]=5000 or 3.7 Log 10 CFU/sample

If no colonies appeared on the test agar plate subculture then the microbial counts were assumed to be less than 1000 due to the dilution factor.

Results

Validation of Test Parameters:

There was less than a 5% difference in the number of organisms recovered from inoculated D/E broth exposed to either the control or test samples prior to plating. If there was any carry-over of triclosan the D/E broth appears to have successfully quenched its antimicrobial properties.

ASTM Method E2315-03 In Vitro Time Kill Assays:

TABLE 1

Results expressed as % reduction of microbes in the test group versus the control group after a 15 second exposure.

| Challenge Organism | Control Sample cfu/sample | Test Sample: EQL-NN-1 cfu/sample | % reduction |
|---|---|---|---|
| Staphylococcus aureus ATCC # 6538 | $7.12 \times 10^6$ | $<10^3$ | >99.99 |
| Pseudomonas aeruginosa ATCC # 9027 | $9.8 \times 10^6$ | $<10^3$ | >99.99 |
| Escherichia coli ATCC # 8739 | $2.7 \times 10^6$ | $<10^3$ | >99.96 |
| MRSA ATCC # 33592 | $5.4 \times 10^6$ | $<10^3$ | >99.98 |
| Aspergillus brasiliensis ATCC 16404 | $3.4 \times 10^5$ | $<10^2$ | >99.97 |
| Candida albicans ATCC 10231 | $4.7 \times 10^5$ | $<10$ | >99.99 |

TABLE 2

Results expressed as Log 10 reduction in microbial counts in the test groups compared to those in the control group after a 15 second exposure.

| Challenge Organism | Control Sample Log 10 cfu/sample | Test Sample: EQL-NN-1 Log 10 cfu/sample | Log 10 reduction |
|---|---|---|---|
| Staphylococcus aureus ATCC # 6538 | 6.85 | <3.0 | >3.85 |
| Pseudomonas aeruginosa ATCC # 9027 | 6.99 | <3.0 | >3.99 |
| Escherichia coli ATCC # 8739 | 6.43 | <3.0 | >3.43 |
| MRSA ATCC # 33592 | 6.73 | <3.0 | >3.73 |
| Aspergillus brasiliensis ATCC 16404 | 5.53 | <2.0 | >3.53 |
| Candida albicans ATCC # 10231 | 5.67 | <1.0 | >4.67 |

The results indicate that the hair removal composition of this invention (EQL-NN-1) formulation tested in this study meets the criteria for antibacterial and antifungal claims. EQL-NN-1 exhibited a greater than 99.9% or 3 Log 10 reduction of a broad spectrum of organism in 15 seconds.

TABLE 3

Zone of inhibition study using MRSA ATCC # 33592 as the test organism.

| Test Group | Zone of Inhibition (mm) |
|---|---|
| EQL-NN-1 | 21 |
| Control (EQL-NN-0) | 0 |

FIG. 1. Zone of inhibition of EQL-NN-1 against MRSA ATCC #33592.

DISCUSSION AND CONCLUSIONS

One of the major concerns of product manufacturers and end users of beauty products such as salons is the risk of microbial contamination and indeed, outbreaks of infections have been documented. In order to minimize this risk, the industry uses various strategies including preservatives, single use products and cleaning/sanitization procedures.

In the case of the hair removal composition of this invention, the product is kept free of microbial contamination by a combination of chemical preservation and elevated temperatures. This study is designed to validate the efficacy of using a combination of temperature and chemical disinfection in reducing or eliminating a broad spectrum of pathogenic organisms.

The hair removal composition of this invention that was tested contained 0.3% triclosan uniformly dispersed throughout the product. Triclosan is a phenolic-based antimicrobial that is commonly found in a variety of consumer products such as soaps, deodorants and toothpaste. Although triclosan is slow acting, it appears that when tested at higher temperatures such as in a range of 68° C. to 72° C. as was done in this study, the antimicrobial activity of the product is greatly enhanced so that a significant reduction in pathogens levels is achieved within 15 seconds.

In conclusion, it appears that when the hair removal composition of this invention was used as directed in a salon setting, any potential pathogenic organism introduced into the product will be rapidly inactivated in 15 seconds or less. The results of this in vitro study validate that hair removal composition of this invention formulated with triclosan was rapidly self disinfecting.

In addition, the antimicrobial hair removal composition of this invention shows good activity against Methicillin resistant Staphylococcus aureus (MRSA) as demonstrated by a large zone of inhibition. MRSA is prevalent in healthcare facilities and appears to be spreading into the general community. Triclosan has been shown to be an efficacious agent for controlling outbreaks of these pathogens.

As this and previous studies have shown, use of the hair removal composition of this invention antimicrobial has a very low probability of transmission of pathogens via cross contamination in the salon setting.

What is claimed:

1. A non-aqueous antibacterial hair removal composition comprising botanical oils and rosins, an amount of solubilizing oil and an antibacterial agent benzethonium chloride in an amount about 0.1% to about 2.0% by weight of the hair removal composition,
   wherein the amount of botanical oils and rosins in the non-aqueous hair removal composition are sufficient that when the hair removal composition is applied to a person's skin and subsequently removed, hair on the skin is entrapped in the hair removal composition and removed therewith; and
   wherein the amount of solubilizing oil is effective for solubilizing the amounts of botanical oils and rosins and antibacterial agent.

2. A non-aqueous antibacterial hair removal composition comprising:
   a. An amount of solubilizing oil;
   b. An amount of soybean oil;
   c. An amount of gum rosin;
   d. An amount of rosin esters;
   e. antibacterial agent benzethonium chloride in an amount of about 0.1% to about 2% by weight of the hair removal composition,
   wherein the amount of soybean oil, gum rosin and rosin esters in the non-aqueous hair removal composition are sufficient that when the hair removal composition is applied to a person's skin and subsequently removed, hair on the skin is entrapped in the hair removal composition and removed therewith; and wherein the amount of solubilizing oil is effective for solubilizing the amounts of soybean oil, gum rosin, rosin esters and antibacterial agent.

3. The hair removal composition of claim 1, wherein the solubilizing oil is mineral oil.

4. The hair removal composition of claim 1, further comprising a colorant.

5. The hair removal composition of claim 1, further comprising an effective amount of fragrance.

6. The hair removal composition of claim 1, further comprising an amount of titanium dioxide.

7. The hair removal composition of claim 1, wherein the hair removal composition is liquid at temperatures above 25° C. (77° F.).

8. A non-aqueous antibacterial hair removal composition comprising:
   a. An amount of solubilizing oil of about 6.0% to about 8.0%, wherein the solubilizing oil is mineral oil;
   b. An amount of soybean oil of about 12.0% to about 16.0%;
   c. An amount of gum rosin of about 6.0% to about 8.0%;
   d. An amount of rosin esters of about 68% to about 72%;
   e. An amount of titanium dioxide of about 0.1%% to about 0.3%;
   f. An antibacterial agent benzethonium chloride in an amount of about 0.1% to about 2.0% by weight of the hair removal composition
   wherein the amounts of soybean oil, gum rosin and rosin esters in the non-aqueous hair removal composition are sufficient that when the hair removal composition is applied to a person's skin and subsequently removed, hair on the skin is entrapped in the hair removal composition and removed therewith; and
   wherein the solubilizing oil is mineral oil and the amount of solubilizing oil is effective for solubilizing the amounts of soybean oil, gum rosin, rosin esters and antibacterial agent.

9. A process of manufacturing the non-aqueous antibacterial hair removal composition of claim 1, comprising:
   a. Heating about one-half the amount of soybean oil to a temperature of from about 85° C. (about 185° F.) to about 95° C. (about 203° F.) to produce a heated soybean oil;
   b. Mixing the amount of gum rosin in the heated soybean oil to produce an initial emulsified composition;
   c. Adding with constant stirring the remaining amount of soybean oil to the emulsified composition to produce a final emulsified composition;
   d. Cooling the final emulsified composition a temperature of about 80° C. (about 176° F.) to about 85° C. (about 185° F.) to produce a cooled final emulsified composition;
   e. Mixing the amount of rosin esters into the cooled final emulsified composition for a period of at least one hour to produce a mixed composition;
   f. Cooling the mixed composition to about 60° C. (about 140° F.) to about 70° C. (about 158° F.) to produce a cooled mixed composition;
   g. Mixing the amount of mineral oil and the amount of benzethonium chloride;
   h. Mixing the second emulsion with the cooled mixed composition for a period of from 2 to 6 hours and subsequently cooling to room temperature to produce the non-aqueous antibacterial hair removal composition.

10. The process of claim 9, wherein the second emulsion further includes an amount of titanium dioxide.

11. A process of manufacturing the non-aqueous antibacterial hair removal composition of claim 9, comprising:
   a. Heating about one-half the amount of soybean oil to a temperature of from about 85° C. (about 185° F.) to about 95° C. (about 203° F.) to produce a heated soybean oil;
   b. Mixing the amount of gum rosin in the heated soybean oil to produce an initial emulsified composition;
   c. Adding with constant stirring the remaining amount of soybean oil to the emulsified composition to produce a final emulsified composition;
   d. Cooling the final emulsified composition a temperature of about 80° C. (about 176° F.) to about 85° C. (about 185° F.) to produce a cooled final emulsified composition;
   e. Mixing the amount of rosin esters into the cooled final emulsified composition for a period of at least one hour to produce a mixed composition;
   f. Cooling the mixed composition to about 60° C. (about 140° F.) to about 70° C. (about 158° F.) to produce a cooled mixed composition;
   g. Mixing the amount of mineral oil and the amount of benzethonium chloride and titanium dioxide to produce a second emulsion;
   h. Mixing the second emulsion with the cooled mixed composition for a period of from 2 to 6 hours and subsequently cooling to room temperature to produce the non-aqueous antibacterial hair removal composition.

12. The non-aqueous antibacterial hair removal composition of claim 1, further including 0.05% to about 3.0% of thyme oil.

13. The non-aqueous antibacterial hair removal composition of claim 1, further including an effective amount of a preservative of phenoxyethanol.

* * * * *